United States Patent [19]

Schneditz

[11] Patent Number: 5,830,365
[45] Date of Patent: Nov. 3, 1998

[54] MEANS FOR DETERMINING HEMODYNAMIC PARAMETERS DURING EXTRACORPOREAL BLOOD TREATMENT

[75] Inventor: Daniel Schneditz, New York, N.Y.

[73] Assignee: Fresenius AG, Germany

[21] Appl. No.: 687,752

[22] Filed: Jul. 25, 1996

[30] Foreign Application Priority Data

Aug. 5, 1995 [DE] Germany .................. 195 28 907.2

[51] Int. Cl.⁶ .................... B01D 17/12; B01D 61/32; G01F 5/00
[52] U.S. Cl. .................. 210/739; 73/861.07; 73/861.18; 128/660.01; 128/668; 210/646; 210/929; 604/4
[58] Field of Search ................. 210/96.2, 143, 210/194, 195.2, 321.65, 645, 646, 739, 742, 929; 604/4–6; 73/40.5 A, 861.18, 861.05, 861.01; 128/660.01, 661.08, 668; 26/87, 90, 741

[56] References Cited

U.S. PATENT DOCUMENTS

| 3,641,994 | 2/1972 | Gosling | 73/861.18 |
| 5,312,550 | 5/1994 | Hester | 210/646 |
| 5,453,576 | 9/1995 | Krivitski | 128/661.08 |
| 5,510,717 | 4/1996 | Buffaloe et al. | 210/646 |
| 5,588,959 | 12/1996 | Ahmad et al. | 604/4 |
| 5,679,245 | 10/1997 | Manica | 210/645 |
| 5,685,989 | 11/1997 | Krivitski et al. | 210/646 |

FOREIGN PATENT DOCUMENTS

| 3720665 | 1/1989 | Germany . | |
| 3720668 | 1/1989 | Germany . | |
| 6-261938 | 9/1994 | Japan | 604/4 |
| 2276566 | 10/1994 | United Kingdom | 604/4 |

OTHER PUBLICATIONS

"Cardiopulmonary recirculation during hemodialysis", Daniel Schneditz et al., Kidney International, Vo. 42 (1992), pp. 1460–1456.

"Color Flow Doppler Predicts PTFE Graft Failure", W Bay, M Henry, E Lowrie, N Lew & NMC DFT Study members, Ohio State University, Columbus, OH and National Medical Care, Inc. (W.R. Grace Company), Waltham, MA.

"Models to Predict Recirculation and Its Effect on Treatment Time in Single–Needle Dialysis", Frank A. Gotch, First International Symposium on Single–Needle Dialysis, edited by S. Ringoir, R. Vanholder, P. Ivanovich, ISAO Press, Cleveland 1984.

"Automated measurement of recirculation", M. Krämer, HD. Plaschegg, EDTNA–ERCA Journal, 19,6 (1993).

"Kontinuierliche Blutvolumenmessung im extrakorporalen kreislauf mit Ultraschall", D. Schneditz et al., Nieren–und Hochdruckkrankheiten, Jahrgang 20, Nr. Nov. 1991, S. 649–652.

Primary Examiner—Joseph W. Drodge
Attorney, Agent, or Firm—Townsend and Townsend and Crew LLP; Kenneth R. Allen

[57] ABSTRACT

The invention relates to a means for determining hemodynamic parameters, such as cardiopulmonary recirculation, fistula flow and cardiac minute output during an extracorporeal blood treatment, in which blood is conducted to a dialyzer (3) by way of arterial branch (8, 8') of extracorporeal path (2) which is fluidly connected to a segment (9, 12) of a fistula (10), then returned by way of venous branch (11, 11') of the extracorporeal path which is fluidly connected to the other segment (12, 9) of the fistula. The hemodynamic parameters are determined by two recirculation fraction measurements taken in quick succession and which are performed automatically by the apparatus before and after the blood flow is reversed. In a computer-memory unit (22) cardiopulmonary recirculation is calculated based on the recirculation fraction during normal blood flow together with the recirculation fraction during reversed blood flow. To determine the recirculation fraction the concentration of an indicator solution is altered in venous branch (11, 11') of the extracorporeal path and the change in concentration of indicator solution resulting from recirculation in arterial branch (8, 8') of extracorporeal path (2) is recorded. In a preferred embodiment of the present invention indicator solution in the form of a predetermined amount of dialyzate is infused into the extracorporeal path by back filtration.

28 Claims, 2 Drawing Sheets

MEANS FOR DETERMINING HEMODYNAMIC PARAMETERS DURING EXTRACORPOREAL BLOOD TREATMENT

BACKGROUND OF THE INVENTION

The invention relates to a means for determining hemodynamic parameters during an extracorporeal blood treatment as is known in U.S. Pat. No. 5,312,550 and which incorporates the use of such a means.

In methods involving repeated purification therapy of the blood, such as hemodialysis, hemofiltration and hemodiafiltration, blood is conducted through an extracorporeal path. To access the vascular system an arterial-venular fistula is frequently surgically attached. An implantation is also possible. All references to "fistula" hereinafter signify any type of connection between a patient's vein and artery, in which the portion of the fistula disposed upstream and closer to the arterial vascular system denotes the arterial segment of the fistula, while the portion of the fistula disposed downstream and closer to the venous portion of the vascular system denotes the venous segment.

Blood flowing through the fistula is only actually used during the dialysis treatment. In the interim period the blood flow corresponds to a functional left/right shunt, in which a portion of the arterial blood from the cardiac minute output (CMO) bypasses peripheral utilization in the shunt and is conducted directly to the venous system and the heart. The fistula flow ($Q_{fi}$) recirculates through the heart and lungs. The fistula flow, since it bypasses the periphery, is also not subject to blood pressure regulation. The systemic blood flow through the peripheral path ($Q_{sys}$) drops by the amount of fistula flow ($O_{sys}$=CMO–$Q_{fi}$), if the cardiac minute output does not increase accordingly. A compensatory increase in the cardiac minute output of this type usually occurs as a result of the increased fistula flow, and it places an increased burden on the patient's blood circulation, not just during hemodialysis.

The fractional portion of fistula flow of the cardiac minute output is defined as cardiopulmonary recirculation.

$$\text{CPR} = \frac{Q_{fi}}{CMO} \qquad \text{Eq. 1}$$

Cardiopulmonary recirculation (CPR) affects not only the patient's circulatory load as a whole, but it also impacts the efficiency of dialysis. Dialyzed blood from the extracorporeal path which bypasses the systemic circulatory regions and is intermixed with the venous return flow from the greater vascular system, leads to a systematic reduction in the concentration of components in arterial blood capable of being dialyzed (D. Schneditz, et al.: Cardiopulmonary recirculation during hemodialysis. Kidney Int. 42:1450–1456, 1992). Thus, it is important to know the extent of cardiopulmonary recirculation.

The perfusion of fistula is important in terms of its functional capability. A drop in the fistula flow ($Q_{fi}$) below a critical value, increases the risk of a fistula thrombosis with the potential loss of access to the vessel (W. Bay, et al.: Colorflow Doppler predicts PTFE graft failure. J. Am. Soc. Nephrol. 5:407,1994), thus adding a significant complication to the dialysis treatment.

Fistula flow that is insufficient and less than the extracorporeal blood flow (Qb) during hemodialysis treatment causes local fistula recirculation, in which a fraction of the dialyzed blood which has been returned to the fistula via the venous blood line is directed via the arterial blood line back to the dialyzer or filter. Such (local) fistula recirculation reduces significantly the efficiency of the dialyzer (F. Gotch: "Models to predict recirculation and its effect on treatment time in single-needle dialysis" First Int. Symposium on Single-Needle Dialysis, Publ.: S. Rignoir, R. Vanholder and P. Ivanovich, Cleveland, ISAO Press, 1984, pages 47–62). Not unexpectedly, such recirculation is frequently encountered in the case of high extracorporeal blood flow.

Given the clinical significance thereof, a number of methods are known for measuring recirculation and the fistula flow. These methods depend on manual injection of an indicator and on manipulation of the dialysis apparatus. EDTNA-ERCA Journal 19,6 (1993) describes, on the other hand, a method known as thermodilution for measuring recirculation, in which a treatment variable is used as an indicator, allowing measurement of recirculation to be performed automatically by the dialysis apparatus. In the known method a brief temperature drop is triggered in the dialysis flow path which is transferred to the venous path. In a known embodiment thereof, the method records the sum of local fistula recirculation and cardiopulmonary recirculation. A venous temperature sensor is used to measure the peak temperature, temporally integrate it and subsequently compare it to the temperature registered in the arterial temperature sensor. The ratio of both temperature integrals serves as a measure for the overall efficiency loss of the dialysis treatment due to fistula and cardiopulmonary recirculation and is referred to hereinafter as recirculation fraction (R). However, measuring the cardiopulmonary recirculation (CPR) and the clinically significant fistula flow ($Q_{fi}$) presents technical difficulties.

A means for determining hemodynamic parameters during an extracorporeal blood treatment is also known from the above mentioned U.S. Pat. No. 5,312,550. During the extracorporeal blood treatment blood is conducted through the arterial branch of the extracorporeal path which is in fluid communication with a section of the fistula, into the dialyzer, then returned through the venous branch of the extracorporeal path which is connected to another section of the fistula. An injection point is disposed in the venous branch of the extracorporeal path for an injection device which enables a substance for altering the properties of the blood to be injected into the venous branch. A measuring device is disposed in the arterial branch of the extracorporeal path and is used to detect changes in the physical property of the blood resulting from recirculation in the fistula.

According to the definition of cardiopulmonary recirculation (CPR), data on the cardiac minute output and the fistula flow are required. In a known method for determining cardiac minute output an indicator solution is injected into the venous line of the extracorporeal path, and the dilution curve in the arterial blood line is then measured (D. Schneditz, et al.: Continuous blood volume measurement in extracorporeal blood path using ultrasound", Nieren- und Hochdruckkrankheiten ([kidney and high blood pressure diseases]) 20:649–652, 1991). The cardiac minute output is then determined from the dilution curve. For recording the dilution curve according to the known method, an ultrasound measuring system is used, which is attached to the arterial line of the extracorporeal path. The fistula flow ($Q_{fi}$) is determined by switching the arterial and venous blood line to the fistula thereby forcing fistula recirculation, then measuring the dilution curve and injecting the indicator solution. Recirculation occurring when the arterial and venous lines to the fistula are switched is hereinafter referred to as "forced fistula recirculation".

SUMMARY OF THE INVENTION

According to the invention, a means is provided that allows hemodynamic parameters to be determined with sufficient accuracy and without manual intervention during an extracorporeal blood treatment, and to provide a method for operating an extracorporeal blood treatment apparatus which permits hemodynamic parameters to be determined with sufficient accuracy during blood treatment.

The object of the invention is achieved with the combination of:

a first device for reversing the blood flow in an extracorporeal path in such a way that during normal blood flow the arterial branch of the extracorporeal path is fluidly connected to the arterial segment of the fistula and the venous branch is fluidly connected to the venous segment and that during reversed blood flow the arterial branch (8') of the extracorporeal path is fluidly connected to the venous segment of the fistula and the venous branch of the extracorporeal path is fluidly connected to arterial segment of fistula, a second device for altering the physical-chemical property of the blood in a branch of the extracorporeal path, which defines the venous branch before or after the blood flow is reversed, a measuring device for measuring the physical or chemical characteristic in a branch of the extracorporeal path, which defines the arterial branch before or after the blood flow is reversed, a control unit linked to the second device for altering the physical or chemical characteristic and to the first device for reversing the blood flow in such a way that a change in the physical or chemical characteristic of aterial blood can be measured before and after the first device to reverse the blood flow in extracorporeal path, and a computer-memory unit to calculate a first recirculation fraction ($R_n$) by deriving a quotient based on the change of physical or chemical characteristic of the aterial blood of the branch of the extracorporeal path and the change of physical or chemical characteristic in the venous branch of extracorporeal path before reversing the blood flow in the extracorporeal path, and to calculate a second recirculation fraction ($R_x$) by deriving a quotient based on the change of a physical or chemical characteristic and the change of physical or chemical characteristic in venous blood after reversing the blood flow in the extracorporeal path, and to calculate cardiopulmonary recirculation (CPR) based on established recirculation fractions ($R_n$, $R_x$) during normal and reversed blood flow ($Q_{b,n}$ and $Q_{b,x}$).

In the claimed apparatus determination of hemodynamic parameters rests on two recirculation measurements taken automatically by the apparatus in rapid succession, before and after reversal of the blood flow in the extracorporeal path. Recirculation fractions (R) and extracorporeal blood flows ($Q_b$) for normal flow direction ($R_n$, $Q_{b,n}$) and reversed flow direction $R_x$, $Q_{b,x}$) in the entire or in portions of the extracorporeal path only are calculated and stored. Assuming that the fistula flow and the cardiac minute output do not change significantly during the period of observation, it is possible to calculate with sufficient accuracy the cardiopulmonary recirculation from the stored values for recirculation fractions ($R_n$, $R_x$) and blood flows ($Q_{b,n}$, $Q_{b,x}$).

It is feasible to incorporate the means for determining hemodynamic parameters in known hemodialysis apparatuses, in which components integral to known hemodialysis apparatuses can be utilized.

The claimed apparatus has a measuring device for determining a physical-chemical property of the extracorporeal blood, which is arranged in the arterial branch of the extracorporeal path, that is, in the branch in which the blood flows from the patient to the dialyzer or filter of the blood treatment apparatus. Further, the apparatus of the present invention has a means for altering the physical-chemical property of the blood in the venous branch of the extracorporeal path, that is, in the branch in which the blood flows from the dialyzer or filter back to the patient, and a means for reversing the extracorporeal blood flow. The means for reversing the blood flow is designed so that once activated, the arterial branch of the extracorporeal path is fluidly connected to venous segment of the fistula disposed downstream thereof, and the venous branch of the extracorporeal path is fluidly connected to the arterial segment of the fistula disposed upstream thereof.

The measuring sequence is automatically controlled by means of a control unit linked to the means for altering the physical-chemical property and to the device for reversing the blood flow in such a way that the change in the physical-chemical property in the arterial branch of the extracorporeal resulting from the forced change in the physical-chemical property in the venous branch, can be measured before and after reversal of the blood flow in the extracorporeal path. The values obtained are then recorded in a computer memory. The recirculation fractions in normal and reversed blood flow are then calculated by computer based on the change in the physical-chemical property in the venous branch of the extracorporeal path known by its magnitude and on the recorded change in the physical-chemical property in the arterial branch of the extracorporeal path. The recirculation fraction is calculated by deriving a quotient based on the change of physical-chemical property in the influx and outflow in the extracorporeal path. Here it is irrelevant whether the change of physical-chemical property in the arterial branch of the extracorporeal path is the result of local fistula recirculation, forced fistula recirculation or cardiopulmonary recirculation.

At this point the cardiopulmonary recirculation is calculated by computer based on the stored recirculation fraction of the normal blood flow and the stored recirculation fraction of the reversed blood flow.

The subclaims are directed to alternate embodiments of the present invention. If the change of physical or chemical characteristic in the venous branch of the extracorporeal path is known by its magnitude, then only one measuring device is needed to measure the physical or chemical characteristic in the arterial branch of the extracorporeal path. In an advantageous embodiment of the present invention a second measuring device is provided for measuring the physical-chemical property in the venous branch of the extracorporeal path. This measuring device can be used to determine the change in physical or chemical characteristic in the venous branch of the extracorporeal path by its magnitude.

Recirculation can be measured in normal and reverse blood flow using known measurement methods. For instance, recirculation may be detected by means of an indicator solution, that is injected into the extracorporeal path. It is feasible to use an indicator solution in the form, e.g. of a tempered, isotonic saline solution having acoustic properties that differ from those of blood. Alternatively, by using a device for altering the physical or chemical characteristic, it is also possible to generate a temporary change in temperature, preferably a temperature drop in the dialyzer fluid path, which is transmitted to the venous blood return, and which causes a change in temperature in the arterial branch of the extracorporeal path as a result of recirculation.

In an embodiment in which the recirculation fraction is determined with a temperature bole in the venous branch of the extracorporeal path resulting from a forced change of temperature in the dialyzer fluid path, a temperature sensor is disposed in the venous branch of the extracorporeal path for determining the magnitude of the jump in temperature and a temperature sensor is also disposed in the arterial branch of the extracorporeal path for determining the resulting temperature change.

In an embodiment in which an indicator solution differing from blood in its acoustic properties is added to the extracorporeal path, the physical or chemical characteristic is advantageously determined by means of an ultrasound measuring device which detects a change in the diffusion rate of ultrasound in the blood based on a change in concentration of indicator solution, as discussed in H. Heimel, et al., Austrian Patent 380339 "Method And Apparatus For Studying Properties of Fluid", 1983. Since the diffusion rate of ultrasound in blood depends on the compressibility and density of the medium, measuring the mass density in accordance with another known method is a possible variant of the measuring device (O. Kratky, et al., "Measuring Fluid and Gas Density Using 10-6 g/cm by 0.6 $cm^3$ Sample Volumes", Z. Angew. Physik 27:273–277, 1969).

When using indicator solutions which alter the optical properties of the blood in the visible, infrared and ultraviolet ends of the spectrum depending upon their concentration, it is generally preferable to draw on the extinction and reflection properties of the blood in the venous and arterial lines for purposes of measuring concentration. When using indicator solutions which alter the electrical properties of blood depending upon their concentration, it is preferable to draw on the conductivity of the blood in the arterial and venous blood lines for purposes of measuring concentration.

When manually injecting an indicator solution, regulating the dosage and tempering the solution have proven problematic. Moreover, there is a risk of switching the solution and of contamination. Instead of injecting a known quantity of indicator solution directly into the venous tube system, a particular advantageous embodiment of the present invention provides for infusion of dialyzate via the dialyzer into the extracorporeal path by means of back filtration. In this case the device for changing the physical or chemical characteristic is designed in such a way that it permits a temporary increase in the hydrostatic pressure in the dialyzer fluid portion of the blood treatment apparatus to thereby feed a predetermined quantity of dialyzate via back filtration into the extracorporeal path. In dialysis apparatuses operating with volumetric balancing the back flow of dialyzate from the dialyzer is temporarily reduced or cut off which allows an increase in hydrostatic pressure to occur in the dialyzer fluid portion. In the dialysis apparatuses it is preferable to employ dialzyers which have suitable properties for adsorbing pyrogenes thereby keeping the injected volume sterile. The composition and temperature of the indicator solution corresponds to that of the dialyzate and are machined monitored in known blood treatment apparatuses. The quantity and pulse rate result from the balancing of the dialyzate flow. When using high-flux dialyzers with small ultrafiltration coefficients, the rate of volumes injected will reach 10 ml/sec.

The flow may be reversed in portions of the extracorporeal path or throughout the entire path. To reverse the flow in portions of the extracorporeal path a switching device in the form of a dual switch is used which is arranged in both branches of the extracorporeal path. Preferably, the flow is reversed immediately proximate the fistula, that is, upstream of the arterial pump located in the extracorporeal path and downstream of a venous tube clamp generally arranged in the extracorporeal path of a blood treatment apparatus, thus allowing the use of security systems normally available in known blood treatment apparatuses. Measuring devices for recording transluminal concentration and temperature measurements are then advantageously arranged at sections of the extracorporeal tube system located on the fistula side.

Alternatively, it is also possible to reverse the blood flow throughout the entire extracorporeal path. In such a case the device for reversing the flow of blood is designed so that the flow direction of the blood pump in the extracorporeal path is reversible. Preferably, arterial and venous monitoring of pressure, deaeration and air in the extracorporeal path is provided.

The claimed device and its use in a blood treatment apparatus not only make it possible to determine cardiopulmonary recirculation, but also to ascertain additional, relevant hemodynamic parameters, such as fistula flow and cardiac minute output during an extracorporeal blood treatment.

BRIEF DESCRIPTION OF THE DRAWINGS

Two preferred embodiments of the present invention are described in greater detail below with reference to the drawings, in which.

DESCRIPTION OF SPECIFIC EMBODIMENTS

Figure 1:
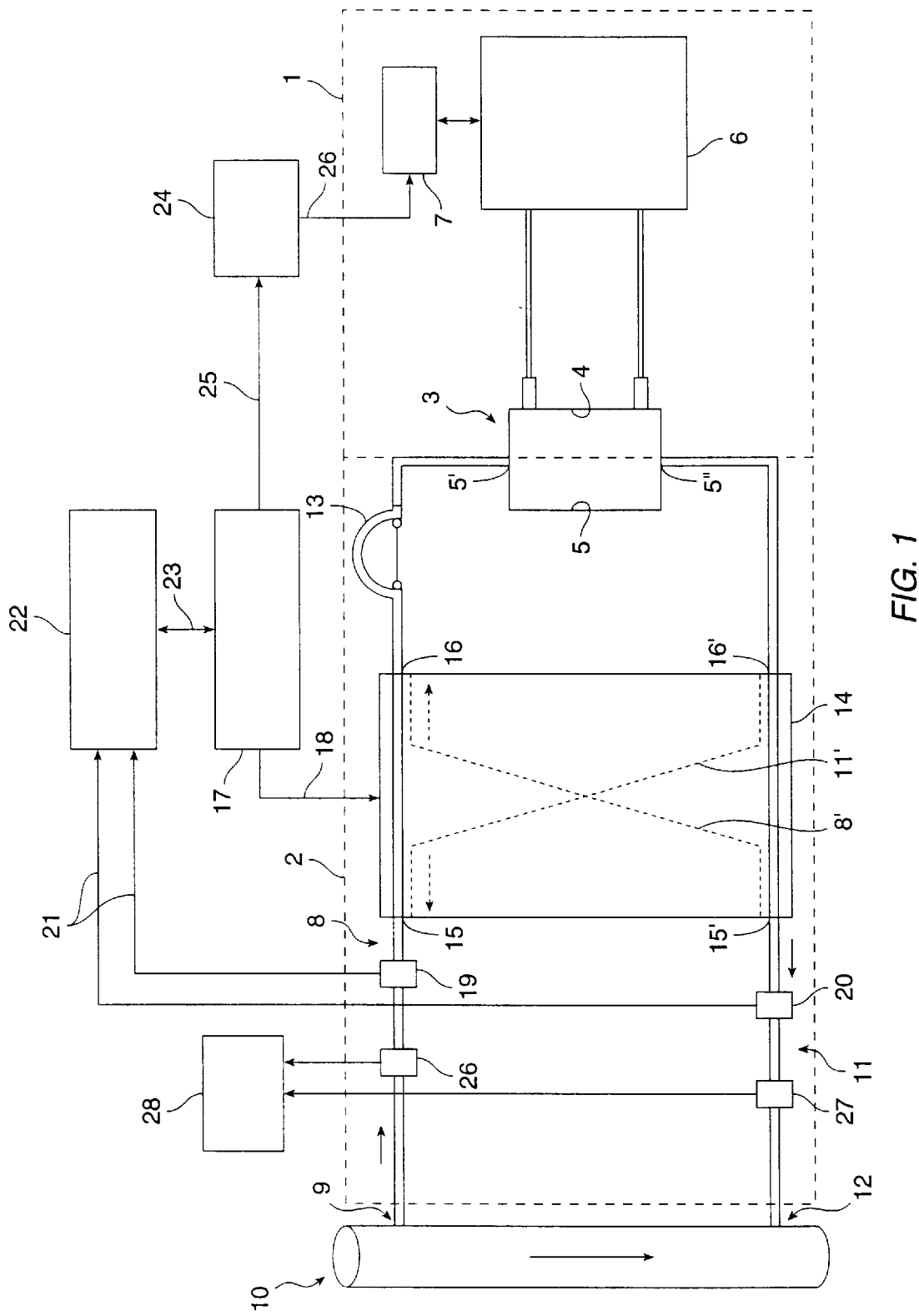
FIG. 1 is a schematic representation of the means for determining hemodynamic parameters in conjunction with the essential components of a hemodialysis apparatus.

FIG. 1 shows an means for determining hemodynamic parameters together with a hemodialysis apparatus. Hereinafter the means will be described as a separate component, although it can be incorporated in the hemodialysis apparatus, particularly since a number of its components are found in known hemodialysis apparatuses. The hemodialysis apparatus comprises essentially a dialysis solution portion 1 and an extracorporeal blood path 2 between which a dialyzer 3 consisting of a dialysis solution chamber 4 and a blood chamber 5 is arranged. The dialysis solution portion 1 has a volumetric balancing system of known design. The known components 6 of dialysis solution portion 1 that are connected to the inlet and outlet of the dialysis solution chamber, are only cursorily indicated in FIG. 1. A control unit for the individual components is indicated in FIG. 1 by reference numeral 7.

The extracorporeal blood path comprises a first blood line that is fluidly connected to the arterial, upstream segment 9 of fistula 10 of the patient and to inlet 5' of the blood chamber 5 of dialyzer 3, and is connected to a second blood line which is fluidly connected to outlet 5" of blood chamber 5 and to venous segment 12 of fistula 10. During normal blood flow the first line defines an arterial branch, that is, the branch that conducts blood to the dialyzer, and the second line defines a venous branch, that is the branch that conducts blood from the dialyzer to the patient. In the first line 8 of extracorporeal path a blood pump 13 is arranged upstream of the dialyzer when the direction of flow is normal. In the normal flow direction blood 13 of the patient drawn from arterial segment 9 of fistula 10 is conducted through the arterial branch 8 of extracorporeal path 2 into blood chamber 5 and is then returned through venous branch 1 to venous segment 12 of fistula 10.

The means for determining hemodynamic parameters incorporates a device 14 arranged in the extracorporeal path for reversing the flow of blood. In the embodiment shown in FIG. 1 the device 14 for reversing the flow of blood is an electromagnetically activated switch having two inputs 15, 15' and two outputs 16, 16', in which the inputs are connected to the parts of the first and second blood lines leading to the patient and the outputs are connected to the parts of the first and second blood lines leading to dialyzer 3. The switch device 14 is constructed so that it is possible to either connect the first input 15 to the first output 16 and the second input 15' to the second output 16', or to connect the first input 15 to the second output 16' and the second input 15' to the first output 16. Once the switch device 14 is activated to reverse the blood flow, venous branch 11' which conducts the blood away from dialyzer 3 is fluidly connected to arterial segment 9 of fistula 10 and branch 8' which conducts blood to dialyzer 3 is fluidly connected to venous segment 12 of fistula 10. A control unit 17 regulates by way of control line 18 switch device 14 used to reverse the blood flow.

The device also has sensors 19, 20, one arranged in the first line and one arranged in the second line of the extracorporeal path for measuring the concentration of an indicator solution which is injected into the extracorporeal path and which differs from blood in its acoustical properties. Sensors 19, 20 are of known design and are based on an ultrasound measuring technique. The diffusion rate of ultrasound in the blood is determined and a change in said diffusion rate is used to deduce a change in concentration of the indicator solution in the blood. Ultrasound sensors 19, 20 are linked by data lines 21 to a computer-memory unit 22 which is connected by a control line 23 to a control unit 17.

The means for determining hemodynamic parameters further comprises a device 24 for automatically injecting a predetermined quantity of dialyzate as an indicator solution into the extracorporeal path 2. Said device is connected by control line 25 to control unit 27, and is also connected by control line 26 to control unit 7 of the hemodialysis apparatus. Device 24 for automatically injecting indicator solution is coupled to control unit 7 of the hemodialysis apparatus in such a way that the return flow of dialyzate out of dialyzer 3 is temporarily reduced or completely cut off, allowing a volume of dialyzate precisely measured by volumetric balancing system 6 to be infused into the extracorporeal path by way of a hydrostatic pressure increase in dialysis solution portion (1). Depending upon the position of switching device 14, the backfiltered volume of dialyzate causes a change in concentration in the venous branch 11 or 11' of the extracorporeal path which is detected by sensors 20 and 19.

When the flow of blood remains unchanged, the backfiltered volume of dialyzate causes an increase in blood flow and blood pressure in venous branch 11 of extracorporeal path 2, and when the blood flow is reversed an increase in blood flow and blood pressure in branch 11' of extracorporeal path 2, which is connected from outlet 5" of blood chamber 5 of dialyzer 3 with the arterial segment 9 of fistula 10 by output 16' and input 15 of device 14. Since increasing the blood flow can alter the recirculation conditions at the vascular opening, the extracorporeal blood flow is preferably lowered by an amount equal to the rate of injection. This is achieved by suitably regulating pump 13 by means of control unit 17 of the hemodialysis apparatus during back filtration of dialyzate.

Located in the segments of the first and second blood line disposed on the fistula side are an arterial and venous pressure measuring device, respectively, an arterial and venous deaerator chamber, an arterial and venous air detector and an arterial and venous tube clamp for immediately detachment of the extracorporeal path from the patient if necessary. Said monitoring and safety devices 26, 27 arranged in both the venous and arterial branch due to the reversal of blood flow are represented only schematically in FIG. 1.

The deaeration chambers allow blood to flow in both directions. Said chamber may be designed, for instance as a modified drip chamber with inlet and outlet tube arranged below the fluid level. The chamber fill level is preferably monitored by a monitoring device 28. In principle both the arterial and venous ultrasound sensors 19, 20 may be used for detecting air. In an embodiment of the aforementioned kind is it not essential to provide separate air detectors in the extracorporeal path. Instead of inserting a separate tube clamp in the first line of the extracorporeal path of the hemodialysis apparatus, it is also feasible to maintain, if necessary, blood pump 13 in the occlusal position.

The means for determining hemodynamic parameters according to the present invention makes use of the following measuring technique:

A change during normal blood flow in the concentration of indicator solution in venous branch 11 of the extracorporeal path 2 due to back filtration of dialyzate $C_{out(0)}$ following $C_{out(1)}$, results in a corresponding change in concentration of $C_{in(0)}$ following $C_{in(1)}$ in arterial branch 8 of extracorporeal path 2 depending upon recirculation, that is, local recirculation and cardiopulmonary recirculation, fistula flow and blood flow. During normal blood flow the outflow of indicator solution from extracorporeal path 2 in the fistula 10 is registered by sensor 20 and the influx of recirculating indicator solution from the fistula into the extracorporeal path is registered by sensor 19. When the blood flow is reversed the tasks of sensors 19 and 20 are reversed relative to measuring the in- and outflow of indicator solution, to the extent that, as shown in FIG. 1, these are found in segments of the extracorporeal path 2 on the patient side which is divided by switching device 14.

The ratio of change in concentration in in- and outflow of the extracorporeal path 2 is indicated by the recirculation fraction:

$$\frac{C_{in(0)} - C_{in(1)}}{C_{out(0)} - C_{out(1)}} = R \qquad \text{Eq. 2}$$

As in other known methods, the recirculation fraction may be determined from the quotient of the quantity of indicator withdrawn from the fistula at location 9 (or 12 when the flow direction is reversed) by the extracorporeal blood flow, and the quantity of indicator solution which flows back to the fistula at location 12 (or 9 when the flow direction is reversed), by integrating the timed concentration curves. Assuming that no significant change occurs in fistula flow $Q_{fi}$ and cardiac minute output during a brief observational span of approximately 10 minutes, the cardiopulmonary recirculation (CPR) is determined by two successive recirculation measurements, in which the first measurement is taken during normal (index n) extracorporeal blood flow $Q_{b,n}$ and the second is taken during reversed (index x) blood flow $Q_{b,n}$ preferably, (though not necessarily) of equal quantity. The cardiopulmonary recirculation CPR is calculated based on recirculation fraction ($R_n$) during normal blood flow and recirculation fraction $R_x$ during reversed blood flow, in addition to the values for both blood flows ($Q_{b,n}$ and $Q_{b,x}$) as follows:

$$CPR = \frac{R_n (1 - R_x)}{R_x (1 - R_n)} \cdot \frac{Q_{b,x}}{Q_{b,n}} \qquad \text{Eq. 3}$$

Given the cardiopulmonary recirculation, the recirculation fraction and the reversed blood flow are determined based on the following equation of the fistula flow $Q_{fi}$ as follows:

$$Q_{fi} = \frac{1 - R_x}{R_x} \cdot \frac{Q_{b,x}}{1 - CPR} \qquad \text{Eq. 4}$$

Alternatively, the fistula flow $Q_{fi}$ can be determined based on the recirculation fraction and the normal blood flow according to the following equation:

$$Q_{fi} = \frac{1 - R_n}{R_x} \cdot \frac{CPR}{1 - CPR} \cdot Q_{b,n} \qquad \text{Eq. 5}$$

If no constituents from the cardiopulmonary recirculation are contained in the dilution curve registered by sensors 19, 20 during reversed blood flow, as for example for rapid transients, and if the dilution curve is measured only to the point at which the cardiopulmonary recirculating indicator constituent impacts the measuring device, equation 4 may be simplified as follows:

$$Q_{fi} = \frac{1 - R_x}{R_x} \cdot Q_{b,x} \qquad \text{Eq. 6}$$

Given the cardiopulmonary recirculation CPR and the fistula flow $Q_{fi}$, the cardiac minute output CMO is calculated according to the following equation:

$$CPR = \frac{Q_{fi}}{CMV}$$

Equations 3 to 5 set forth above apply only when no local fistula recirculation occurs during normal blood flow, that is $Q_{b,n} \leq Q_{fi}$.

The plausibility of the calculated values may be preferably tested in the following way: If the measured recirculation fraction is greater during reversed blood flow than a preferably predetermined maximum value, then CPR, $Q_{fi}$ and CMV are not calculated according to the equations set forth above. An approximate calculation of $Q_{fi}$ is made in accordance with equation 6. In this case, the measurement of the recirculation fraction during normal blood flow ($R_n$) is repeated with a blood flow that is less than the fistula flow calculated according to equation 6. It is advantageous if the maximum value $R_x$ is 0.5, since with any higher value it can be assumed that for the same blood ($Q_{b,n}=Q_{b,x}$) flowing in the normal direction local fistula recirculation will have occurred. Under these latter circumstances equations 3 to 5 are only partially applicable.

The means for determining cardiopulmonary recirculation (CPR) the fistula flow $Q_{fi}$ and the cardiac minute output CMO functions in the following manner.

First control unit 17 signals device 14 to add an indicator solution such that a predetermined quantity of indictor solution in the form of dialyzate is infused into extracorporeal path 2 through dialyzer 3. Venous ultrasound sensor 20 detects at predetermined intervals a change in concentration $C_{out(0)} - C_{out(1)}$ in venous branch 11 of the extracorporeal path resulting from back filtration of dialyzate. Arterial ultrasound sensor 19 also registers at predetermined intervals the change in concentration $C_{in(0)} - C_{in(1)}$ in arterial branch 8 of extracorporeal path 2 resulting from the dilution transition in venous branch 11. The values obtained are then stored in a computer memory unit 22, integrated for the duration of the dilution transients, and recirculation fraction $R_n$ during normal blood flow is then calculated in the computer-memory unit according to equation 2, based on the stored values or on the faces of the dilution peaks and/or indicator quantities. At this point control unit 17 signals device 14 to reverse the flow of blood. The aforementioned values are then registered by ultrasound sensors 19, 20 during reversed blood flow, under which conditions sensor 19 registers the return flow of the indicator solution from the extracorporeal path in section 9 of fistula 10, and sensor 20 registers the influx of recirculating indicator constituents from section 12 of fistula 10 into extracorporeal path 2. The changes in concentration that were measured at predetermined intervals are stored in computer-memory unit 22, then integrated for the duration of the dilution transients, and recirculation fraction $R_x$ during reversed blood flow is calculated using equation 2 and is based on the change of concentration or on the face of the registered dilution peak and/or indicator quantities, then stored in memory. Next, cardiopulmonary recirculation CPR is determined by computer-memory unit 22 using equation 3 and based on stored recirculation fractions $R_n$, $R_x$ during normal and reversed blood flow. Finally, fistula flow $Q_{fi}$ and cardiac minute output CMO are determined using equations 3 to 6 and equation 1. The hemodynamic parameters thus determined are then indicated on a display not shown in FIG. 1.

As measurements are being taken, the pressure in the arterial and venous branch of extracorporeal branch 2 is measured by arterial and venous pressure measuring devices 26, 27 before and after device 14 for reversing the flow of blood is activated and given an identical blood flow $Q_b$, the values obtained are evaluated by a monitoring device 28. In the event the arterial pressure measured by pressure measuring device 27 during reversed blood flow is lower than the arterial pressure measured by pressure measuring device 26 during normal blood flow of equal quantity, and if the venous pressure measured by pressure measuring device 26 during reversed blood flow is higher than the venous pressure measured by pressure measuring device 27 during normal blood flow of equal quantity, then an alarm signal is generated by monitoring device 28. In such a case the cause may be traced to a mechanical blockage in the flow in fistula 10 located between puncture points 9 and 12, requiring correction of the calculated fistula flow $Q_{fi}$.

If the measured recirculation fraction is greater during reversed blood flow than a preferably predetermined maximum value, CPR, $Q_{fi}$ and CMO are not calculated using the equations set forth above. An approximate calculation of $Q_{fi}$ is made using equation 6. In such case, the measurement of the recirculation fraction in the normal flow direction ($R_n$) is repeated with a blood flow that is less than the fistula flow as calculated using equation 6.

Figure 2:
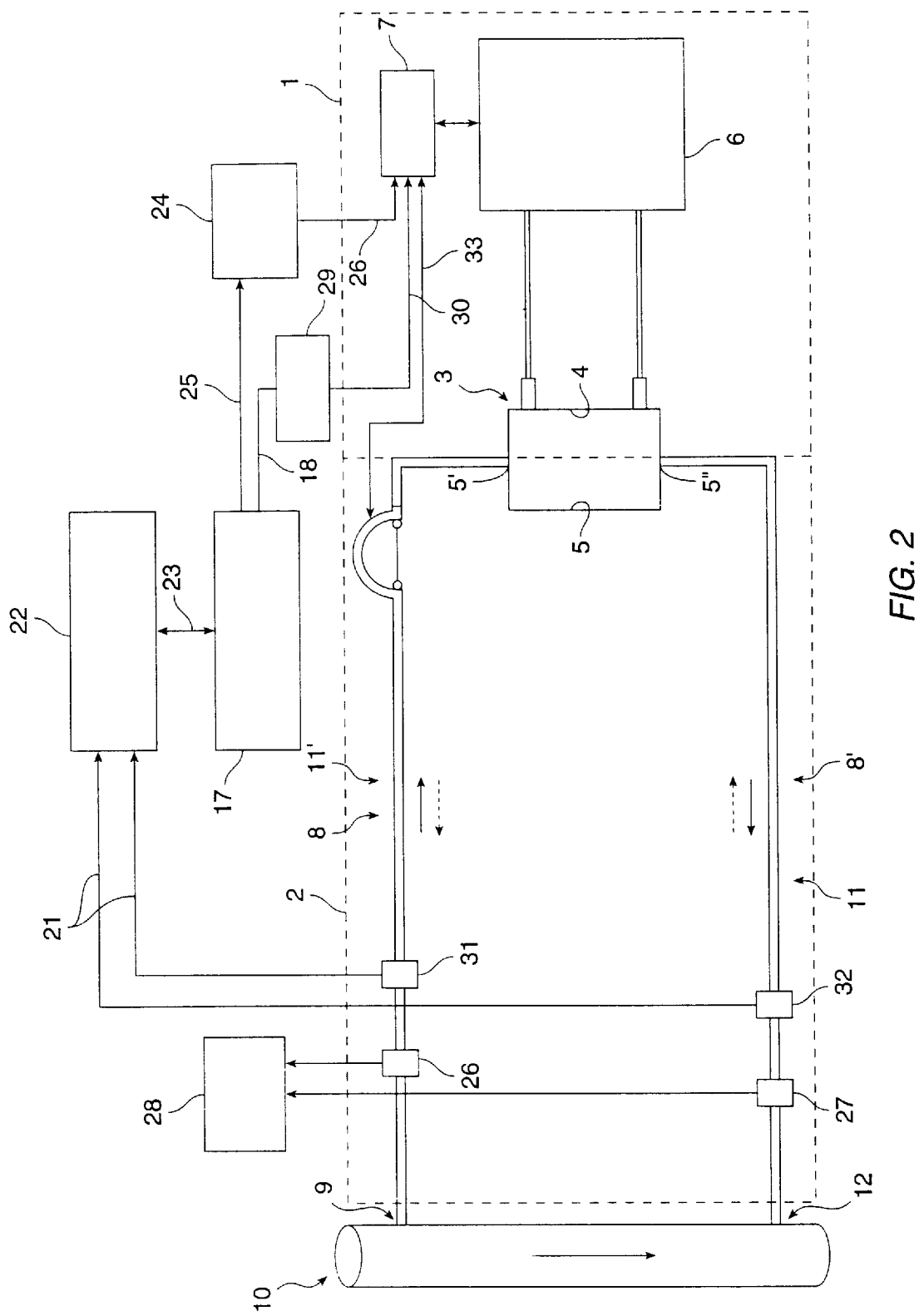
FIG. 2 is a second embodiment of the means.

The embodiment of the means according to the present invention shown in FIG. 2 differs from the embodiment referred to in FIG. 1 in that the device for reversing the blood flow is a switch 29 which reverses the flow direction of the blood pump arranged in extracorporeal path 2. In this case device 29 is connected by a control line 30 to control unit 7 of the hemodialysis apparatus, which sends appropriate signals to blood pump 13 via control line 33. In addition, instead of ultrasound sensors, temperature sensors 31, 32 are arranged in the first and second blood lines of extracorporeal path 2. Instead of backfiltrating an indicator solution in the form of dialyzate, in the embodiment according to FIG. 2 a temperature change is generated in the dialysis solution path 1 by means of device 24 to alter the physical-chemical property, which temperature change is transmitted during normal blood flow to the blood in the second line of extracorporeal path 2, which during normal blood flow is venous branch 11, and during reversed blood flow is transmitted to blood in the first line of the extracorporeal path, which during reversed blood flow is venous branch 11'. Recirculation thus causes a change in temperature in arterial branch 8 and 8' of extracorporeal path 2 during normal and reversed blood flow. The cardiopulmonary recirculation CPR, fistula flow $Q_{fi}$ and the cardiac minute output CMO are then determined from the temperature changes in arterial branch 8 and 8' of extracorporeal path 2 during normal and reversed blood flow in a manner analogous to the ultrasound dilution measurement described above.

The invention has now been explained with reference to specific embodiments. Other embodiments will be apparent to those of ordinary skill in the art from a review of this description. Therefore, it is not intended for this invention to be limited by anything other than a combination of essential elements, of which specific examples are given in the claims.

What is claimed is:

1. An apparatus for determining hemodynamic parameters during an extracorporeal blood treatment in which blood is conducted through a first branch of an extracorporeal blood path which is fluidly connected to an arterial segment of a fistula, into a dialyzer or filter and returned to a second branch of the extracorporeal path which is fluidly connected to a venous segment of the fistula, comprising:

a first device for reversing the blood flow in the extracorporeal path, the first device having two inputs and two outputs so that during normal blood flow a first input is connected to a first output and a second input is connected to a second output, and in reversed blood flow it is activated to reverse the first input is connected to the second output and the second input is connected to the first output;

the first branch comprising:
      a first section having one end connected to the arterial segment of the fistula, and the other end connected to the first input of the first device, and
      a second section having one end connected to the first output of the first device, and the other end connected to the dialyzer or filter;

the second branch comprising:
      a first section having one end connected to the venous segment of the fistula, and the other end connected to the second input of the first device, and
      a second section having one end connected to the second output of the first device, and the other end connected to the dialyzer or filter;

a second device for altering a physical or chemical characteristic of the blood during normal blood flow in the first section of the second branch and for altering the physical or chemical characteristic of the blood during reversed blood flow in the first section of the first branch;

a measuring device for measuring the physical or chemical characteristic of the blood during normal blood flow in the first section of the first branch and during reversed blood flow in the first section of the second branch;

a control unit linked to the second device for altering the physical or chemical characteristic of the blood and to the first device in such a way to enable measuring changes in the physical or chemical characteristic of the blood from before to after activating of the first device; and a computer-memory unit for calculating a recirculation fraction by deriving a quotient based on the change of the physical or chemical characteristic of the blood in the first section of the first branch and the change of the physical or chemical characteristic in the first section of the second branch before reversing the blood flow in the extracorporeal path, and for calculating the recirculation fraction by deriving a quotient based on the change of physical or chemical characteristic in the first section of the second branch and the change of physical or chemical characteristic in the first section of the first branch after reversing the blood flow in the extracorporeal path, and for calculating cardiopulmonary recirculation based on established recirculation fractions during normal and reversed blood flow.

2. The apparatus of claim 1, wherein the physical or chemical characteristic of the blood is the concentration of an indicator solution.

3. The apparatus of claim 2, wherein the indicator solution has acoustical properties different from those of blood.

4. The apparatus of claim 2, wherein the measuring device is an ultrasound-measuring device which registers a change in the concentration of the indicator solution in the blood based on a change in the diffusion rate of ultrasound.

5. The apparatus of claim 2, wherein the second device injects a predetermined quantity of the indicator solution in the form of a dialyzate into the extracorporeal path.

6. The apparatus of claim 2, wherein the second device generates a temperature change path of the indicator solution to alter the physical or chemical blood characteristic.

7. The apparatus of claim 1, wherein the physical or chemical blood characteristic is the blood temperature.

8. The apparatus of claim 1, wherein the computer-memory unit computes a fistula flow based on the recirculation fractions and blood flows measured during both normal and reverse flow.

9. The apparatus of claim 8, wherein the computer-memory unit computes a cardiac minute output based on the cardiopulmonary recirculation and the fistula flow.

10. The apparatus of claim 1, further comprising a pressure measuring device in the first section of the first and second branch of the extracorporeal path, and a monitoring device to monitor the pressure in the first section of the first and second branch of the extracorporeal path during normal and reversed blood flow and to generate an alarm signal if the pressure measured during reversed blood flow in the first section of the second branch is lower, and the pressure measured during reversed blood flow in the first section of the first branch is higher than during normal blood flow.

11. The apparatus of claim 1, further comprising a third device coupled to the control unit for sending signals to a pump.

12. An apparatus for determining hemodynamic parameters during an extracorporeal blood treatment in which blood is conducted through a first branch of an extracorporeal blood path which is fluidly connected to an arterial segment of a fistula, into a dialyzer or filter and returned to a second branch of the extracorporeal path which is fluidly connected to a venous segment of the fistula, comprising:

a first device for reversing the blood flow in the extracorporeal path, the first device being a switch which can be activated to reverse the flow direction of the blood pump which is located in the extracorporeal path;

a second device for altering a physical or chemical characteristic of the blood during normal blood flow in the second branch and for altering the physical or chemical characteristic of the blood during reversed blood flow in the first branch;

a measuring device for measuring the physical or chemical characteristic of the blood during normal blood flow in the first branch and during reversed blood flow in the second branch;

a control unit linked to the second device for altering the physical or chemical characteristic of the blood and to the first device in such a way to enable measuring changes in the physical or chemical characteristic of the blood from before to after activating of the first device; and a computer-memory unit for calculating a recirculation fraction by deriving a quotient based on the change of the physical or chemical characteristic of the blood in the first branch and the change of the physical or chemical characteristic in the second branch before reversing the blood flow in the extracorporeal path, and for calculating the recirculation fraction by deriving a quotient based on the change of the physical or chemical characteristic in the second batch and the change of the physical or chemical characteristic in the first branch after reversing the blood flow in the extracorporeal path, and for calculating cardiopulmonary recirculation based on established recirculation fractions during normal and reversed blood flow.

13. The apparatus of claim 12, wherein the physical or chemical characteristic of the blood is the concentration of an indicator solution.

14. The apparatus of claim 13, wherein the indicator solution has acoustical properties different from those of blood.

15. The apparatus of claim 13, wherein the measuring device is an ultrasound-measuring device which registers a change in the concentration of the indicator solution in the blood based on a change in the diffusion rate of ultrasound.

16. The apparatus of claim 13, wherein the second device injects a predetermined quantity of the indicator solution in the form of dialyzate into the extracorporeal path.

17. The apparatus of claim 13, wherein the second device generates a temperature change in the path of the indicator solution to alter the physical or chemical blood characteristic.

18. The apparatus of claim 12, wherein the physical or chemical blood characteristic is the blood temperature.

19. The apparatus of claim 12, wherein the computer-memory unit computes a fistula flow based on the recirculation fractions and blood flows measured during both normal and reverse flow.

20. The apparatus of claim 19, wherein the computer-memory unit computes a cardiac minute output based on the cardiopulmonary recirculation and the fistula flow.

21. The apparatus of claim 12, further comprising a pressure measuring device in the first and second branch of the extracorporeal path, and a monitoring device to monitor the pressure in the first and second branch of the extracorporeal path during normal and reverse blood flow, and to generate an alarm signal if the pressure measured during reversed blood flow in the second branch is lower, and the pressure measured during reversed blood flow in the first branch is higher than during normal blood flow.

22. The apparatus of claim 12, further comprising a third device coupled to the control unit for sending signals to a pump.

23. A method for operating an extracorporeal blood treatment apparatus for determining hemodynamic parameters during extracorporeal blood treatment, in which blood is conducted to a dialyzer or filter of the blood treatment apparatus via an arterial branch of the extracorporeal path which is fluidly connected to an arterial segment of a fistula, and returned via a venous branch of the extracorporeal path that is fluidly connected to a venous segment of the fistula, which includes the following steps:

altering a physical-chemical characteristic of the blood in the venous branch of the extracorporeal path;

measuring the change in the physical-chemical characteristic of the blood in the arterial branch of the extracorporeal path;

calculating the recirculation fraction during normal blood flow by a computer-memory unit by deriving a quotient based on the change in the physical-chemical characteristic of the blood in the arterial branch of the extracorporeal path and the change in the physical-chemical characteristic of the blood in the venous branch of the extracorporeal path;

storing a blood flow value in a memory device;

reversing the blood flow so that the arterial branch of the extracorporeal path is fluidly connected to the venous segment of the fistula and the venous branch of the extracorporeal path is fluidly connected to the arterial segment of the fistula;

altering the physical-chemical characteristic of the blood in the venous branch of the extracorporeal path which is fluidly connected to the arterial segment of the fistula;

measuring the change in the physical-chemical characteristic of the blood in the arterial branch of the extracorporeal path which is fluidly connected to the venous segment of the fistula;

calculating the recirculation fraction during reversed blood flow by a computer-memory unit by deriving a quotient based on the change in the physical-chemical characteristic of the blood in the arterial branch of extracorporeal path which is fluidly connected to venous segment of the fistula, and the change in the physical-chemical characteristic of the blood in the venous branch of extracorporeal path which is fluidly connected to the arterial segment of the fistula;

storing the blood flow value in the memory device; and computing the cardiopulmonary recirculation in the computer-memory unit based on stored values for recirculation fraction and blood flow in the normal flow direction and the stored values for recirculation fraction and blood flow in the reversed flow direction.

24. The method of claim 23, further comprising the step of determining the change in the physical-chemical characteristic of the blood in the venous branch of the extracorporeal path by measuring the magnitude of the physical-chemical characteristic of the blood in the venous branch of the extracorporeal path.

25. The method of claim 23, further comprising the step of determining the concentration of an indicator solution.

26. The method of claim 25, further comprising the step of increasing the hydrostatic pressure in the indicator solution, wherein the indicator solution is a predetermined quantity of dialyzate and is infused into the extracorporeal path by back filtration.

27. The method of claim 25, further comprising the step of changing the temperature of the indicator solution.

28. The method of claim 23, further comprising the step of determining the temperature of the blood.

* * * * *